US00PP12761P2

(12) United States Plant Patent
de Groot

(10) Patent No.: US PP12,761 P2
(45) Date of Patent: Jul. 9, 2002

(54) GARLIC PLANT NAMED 'MELANY'

(75) Inventor: Henk de Groot, Broek op Langedijk (NL)

(73) Assignee: De Groot & Slot Beheer B.V. (DE)

( * ) Notice: Subject to any disclaimer, the term of this patent is extended or adjusted under 35 U.S.C. 154(b) by 0 days.

(21) Appl. No.: 09/325,778

(22) Filed: Jun. 4, 1999

(51) Int. Cl.[7] ..... A01H 5/00
(52) U.S. Cl. ..... Plt./258
(58) Field of Search ..... Plt./258

(56) References Cited

PUBLICATIONS

European Community Application—MELANY (Jun. 24, 1996).
European Community Grant—MELANY (Dec. 15, 1999).
"Garlic Collection", de Groot en Slot (Sep. 1998), The Netherlands.

GTITM UPOVROM Citation for 'Melany' as per QZ PBR 952891; Oct. 9, 1995.*

* cited by examiner

*Primary Examiner*—Bruce R. Campell
*Assistant Examiner*—Kent L. Bell

(57) ABSTRACT

A new and distinct cultivar of garlic plant named 'Melany', characterized by early harvesting of the plant, high yield of bulbs, disease-free vegetation, presence of flower scape, and vigorous foliage that develops quicker and has more volume than comparative cultivars.

4 Drawing Sheets

BACKGROUND OF THE INVENTION

The present invention relates to a new and distinct cultivar of garlic plant, botanically known as *Allium sativum L.* and hereinafter referred to by the cultivar name 'Melany'.

'Melany' is a product of a planned breeding program which had the objective of creating new garlic cultivars having early harvesting capabilities, high yield potential, regular clove arrangements, healthy plant material and seed-propagated garlic cultivation.

'Melany' was originated from an open pollination made in a controlled breeding program, which began in 1986 in Broek op Langedijk, the Netherlands. The parent lines were unnamed seedlings of Chinese origin. During the breeding program, several selections were made within the progeny of the open pollination.

'Melany' was discovered and selected as one plant growing among the group of selected plants by the inventor, Henk de Groot, in 1989 in a controlled environment in Broek op Langedijk, the Netherlands.

The first act of asexual reproduction of 'Melany' was accomplished by the inventor in which cloves were taken from the initial selection in August 1989 in a controlled environment in Broek op Langedjik, the Netherlands. Horticultural examination of asexually reproduced plants of 'Melany' in 1990 has demonstrated that the combination of characteristics as herein disclosed for 'Melany' are firmly fixed and are retained through successive generations of asexual reproduction.

BRIEF DESCRIPTION OF THE INVENTION

The following traits have been repeatedly observed and are determined to be basic characteristics of 'Melany' which in combination distinguish this garlic as a new and distinct cultivar:

1 1. Early harvesting of the plant;

1 2. High yield of bulbs;

1 3. Disease-free vegetation;

1 4. Presence of flower scape; and

1 5. Vigorous foliage that develops quicker and has more volume than comparative cultivars.

'Melany' has not been observed under all possible environmental conditions. The phenotype of the new cultivar may vary significantly with variations in environment such as daylength, temperature, soil condition, humidity, fertilization and date of planting without any change in genotype of the cultivar. The following observations, measurements, and comparisons describe plants grown in Broek op Langedijk, the Netherlands under conditions that approximate those generally used in commercial practice. The age of the plants described is 9 months after planting.

Of the many commercial cultivars known to the present inventor, the most similar in comparison to 'Melany' is 'Sprint' (unpatented). In comparison to 'Sprint', 'Melany' has similar bulb and clove colors but demonstrates significant differences in the earliness of harvesting, higher yield and healthier cultivation.

The following chart represents a comparison, based on Dutch cultivation conditions, of the principle variety characteristics of 'Melany' and 3 main commercial varieties:

| Variety characteristics | 'Thermidrome' | 'California Early' | 'Germidour' | 'Melany' |
|---|---|---|---|---|
| Emergence speed after planting | slow | slow | fast | very fast, approximately 4 to 5 weeks |
| Foliage Aspect | erect | erect | bending up to hanging | leaf hanging |
| Foliage Color | green | green | green | light-green RHS137 C for both upper and lower leaf surfaces |
| Plant Height - normal length of the foliage | 60 cm | 60 cm | 65 cm | 60 cm |
| Plant Height - maximum length of the foliage | 85 cm | 80 cm | 85 cm | 100 cm |
| Strength of the plant | normal | normal | normal | normal |
| Susceptibility to bolt | no | no | no | 26 weeks after planting |
| Tendency for branching | very light sensitive | insensitive | insensitive | very light sensitive |
| Earliness (10 is fastest variety 'Melany', difference in weeks) | 6 | 7 | 8 | 10 |
| Skin color of the bulb | white | white | pink/purple | pink striped 66B |
| Skin color of the cloves | white | white | pink/purple | light-pink, RHS 68D |
| Yield in gram/bulb (average of 2 years) | 80 | 80 | 85 | 95 |
| Yield in ratio to 'California Early'/'Thermidrome' | 100% | 100% | 105% | 120% |
| Average number cloves per bulb | 10 to 12 | 10 to 12 | 9 to 11 | 10 to 12 |
| Clove arrangement | irregular | irregular | irregular | fairly regular |
| Percentage dry matter (average of 3 years) | 40 | 39 | 39 | 33 |
| Storability | medium | medium | medium | short, 8 to 10 weeks after harvesting |

In the above chart, susceptibility to bolt was measured by visual observations based upon the inventor's information from the Dutch trial field during the 1996/1997 and 1997/1998 production seasons. Earliness (10 is fastest variety 'Melany'; difference in weeks) indicates that 'Melany' is considered to be the earliest variety whereby the standard is 10. Therefore, an earliness of 8, as in 'Germidour' (unpatented) for example, means that this variety is 2 weeks slower than 'Melany'. These figures are based upon the inventor's information from the Dutch trial field during the 1996/1997 and 1997/1998 production seasons.

Also, in the above chart, 'Carlifornia Early' (unpatented) and 'Thermidrome' (unpatented) are standard cultivars in the U.S. and Europe, respectively, and can be compared with respect to yield (production weight per area). The percentages that are given for Yield in ratio to California Early/Thermidrome indicates the relative average yield increase of the new cultivar. Dry matter was measured by means of a drying apparatus in which 25 grams of garlic material per variety was dried for 72 hours at 72° C. The percentage of dry matter was then calculated using the formula: 100× weight of material after drying/weight of same material before drying. To determine an average, this test was repeated five times for each growing season 1996/1997 and 1997/1998. Storability was measured as the relative marketable yield relative to garlic bulbs after certain storage periods: 4–6–8 months.

BRIEF DESCRIPTION OF THE DRAWINGS

The accompanying photographic drawings show typical plant and bulb characteristics of 'Melany' following growth from appropriate growing conditions, with colors being as true as possible with illustrations of this type.

Sheet 1 shows a side view of the plant.

Sheet 2 shows a side and bottom view of the bulb.

Sheet 3 shows individual cloves within the bulb.

Sheet 4 is a cross-sectional view of the bulb showing the arrangement of the cloves. 'Melany' was known as "GS 201" during testing, as labeled on the photographic drawings.

DETAILED BOTANICAL DESCRIPTION

The following observations, measurements and values describe the new cultivar as grown in Broek op Langedijk, the Neterlands, under conditions which closely approximate those generally used in commercial practice. Color references are made to The Royal Horticultural Society Colour Chart (R.H.S.), except where general colors of ordinary significance are used.

Origin: Through breeding in Broek op Langedijk, the Netherlands.

Parentage: Unnamed seedlings of Chinese origin.

Classification:

*Botanical.*—*Allium sativum L.*

*Commercial.*—Garlic, c.v. 'Melany'.

Plant:

*Form.*—Bulbous herb.

*Height.*—Normal height of a mature plant is approximately 60 cm, depending on cultivation conditions. Maximum height is approxmately 100 cm. Height including umbel is approximately 100 cm, depending on cultivation conditions when grown in Broek op Langedijk, The Netherlands.

*Growth habit.*—Fast response, very vigorous growth and volume (in comparsion to standard variety 'California Early'.

*Harvest/typical growing season.*—In one growing season only one harvest takes place. The typical growing season is from October to July in Western European climate conditions and from October to June in sub-Mediterranean conditions.

Foliage:

*Quantity.*—11 leaves depending on cultivation conditions.

*Size.*—Minimum leaf length is 60 cm, maximum leaf length is 100 cm, depending on cultivation conditions.

*Shape of leaf.*—Elongated.

*Aspect.*—Arched to hanging.

*Color.*—Light-green RHS 137 C for both upper and lower leaf surfaces.
*Leaf width.*—1–2 cm.
*Apex.*—Acute.
*Base.*—Sessile.
*Texture.*—Glossy.
*Stem coloration.*—Converts from white to green RHS 137 C with pink coloration.

Scape:
*Length.*—150 cm depending on cultivation conditions.
*Diameter.*—Less than 1 cm.
*Color.*—RHS 137 C.

Umbels:
*Length.*—4.5 to 5 cm.
*Diameter.*—5 cm.
*Bracts.*—1; width 1 cm; length 3–4 cm; light green, RHS 142D.
*Bulbils.*—Present more than 50, less than 200, depending on cultivation and climate conditions.
*Shape.*—Elliptical.
*Length.*—5 mm.
*Diameter.*—2 mm.
*Color.*—Brown, approximately RHS 200D.
*Spathe.*—1, Compound flower filled with bulbils (a composition of bulbils and flowers).
*Shape.*—Bulbous, tapered at one side.
*Size.*—4.5–5 cm long; 5 cm in diameter.
*Pedicels.*—Length 3 cm; diameter 1 mm; color green, RHS 143C.

Flower bud:
*Length.*—2 mm.
*Diameter.*—1 to 2 mm.
*Shape.*—Size and form of a pin-head.
*Color.*—Light green base, approximately RHS 142D and green-white head, RHS 157B.

Bulb:
*Shape.*—Round to spherical.
*Size.*—Average of 8 cm in diameter, depending on cultivation conditions.
*Color.*—Striped-pink, RHS 63B.
*Average weight of bulb.*—95 grams over 2 years of research (average weight from two different years).
*Number of cloves.*—10 to 12 depending on cultivation conditions.
*Clove color.*—White RHS 155D.
*Clove skin color.*—Light-pink RHS 68 D.
*Clove shape.*—Transversely in triangular shape with round edges.
*Clove length.*—2–3 cm; in longitudinal section running to a point.
*Clove diameter.*—1–2 cm at the widest part.
*Clove texture.*—Glossy with and without the skin.
*Individual weight of clove.*—Average 12 grams per clove depending on cultivation conditions.

Disease resistance: Very high for mildew, rust and botrytis.

Other characteristics: Dry matter averaged 33% over 3 years of research. Storability short.

Reproductive organs:
*Anthers.*—Quantity: 5–15. Size: Less than 1 mm. Color: Grey.
*Stigma and styles.*—Typical of the species.
*Ovaries.*—Quantity: 8 per flower. Size: 2 mm. Color: Light green and white.
*Pollen.*—None produced.

Seed: None produced.

I claim:

1. A new and distinct cultivar of garlic plant named 'Melany', as illustrated and described.

* * * * *

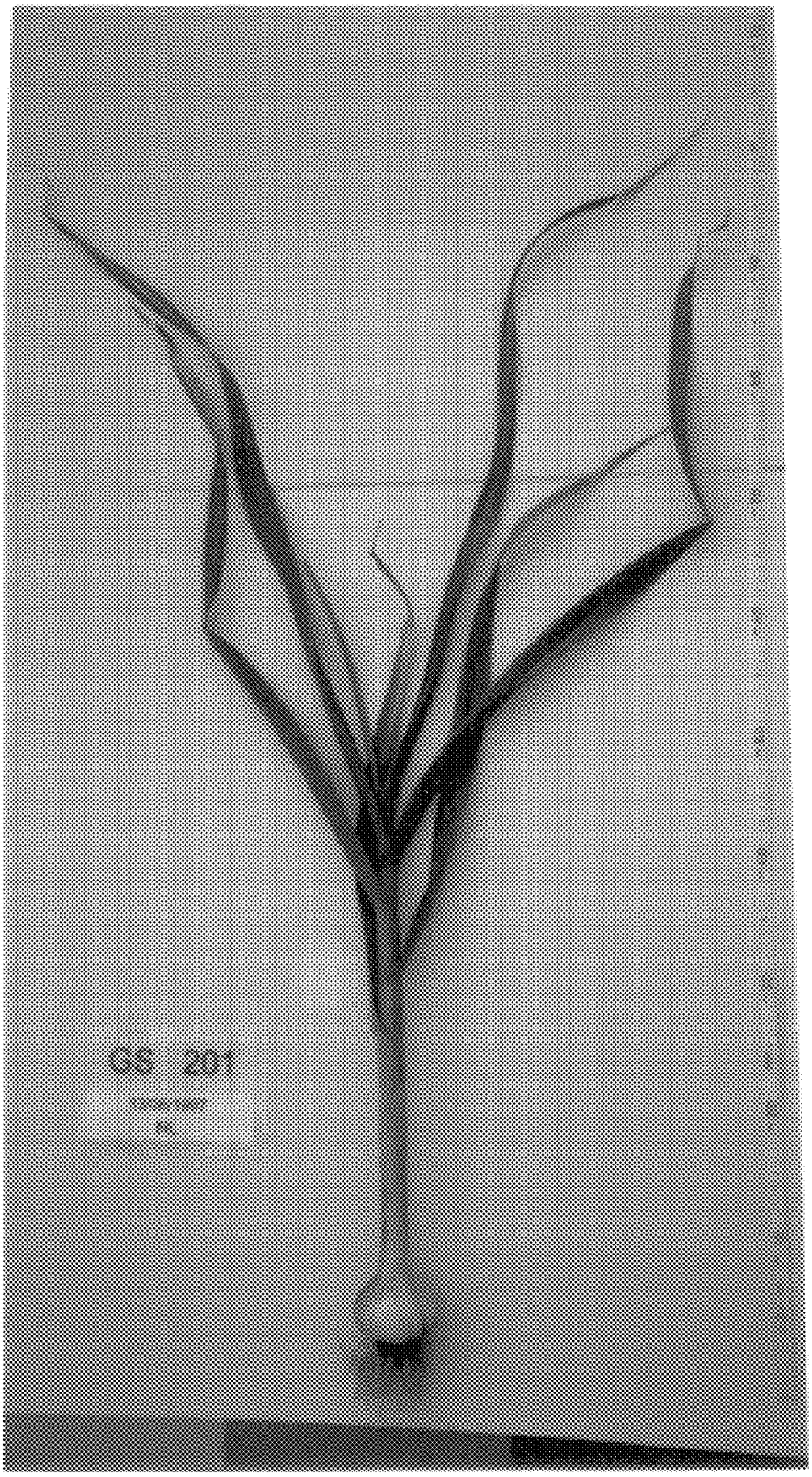
GS 201

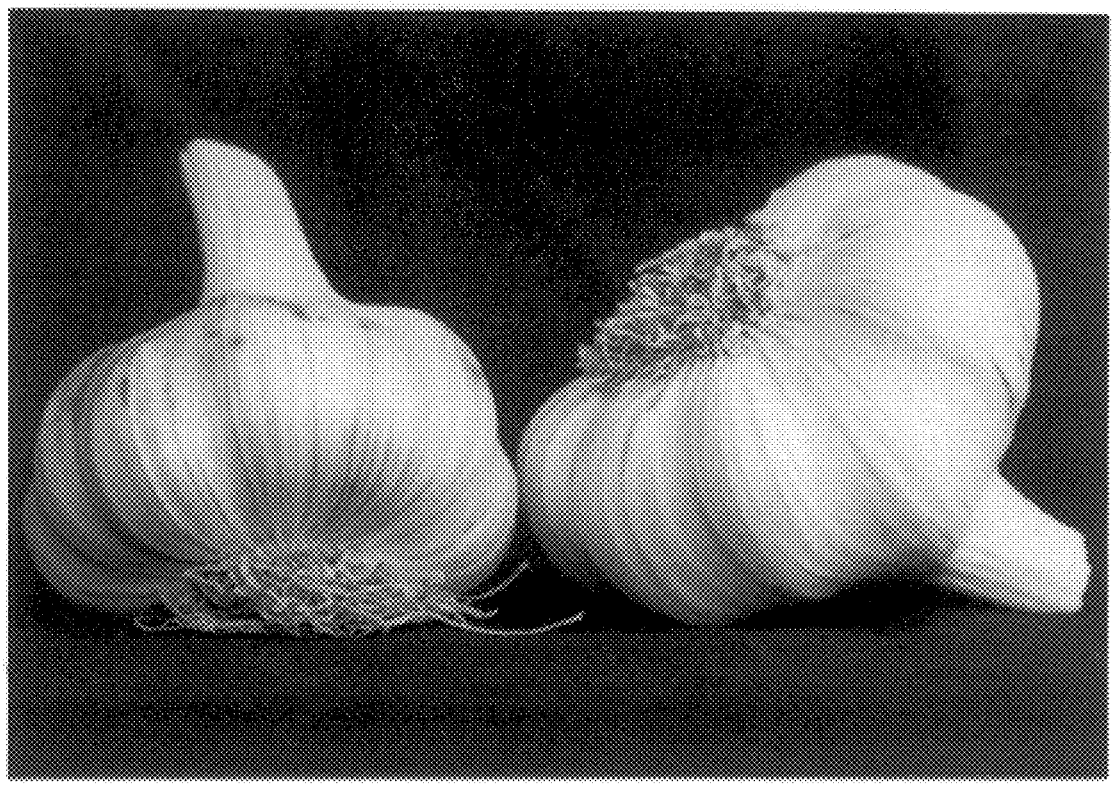

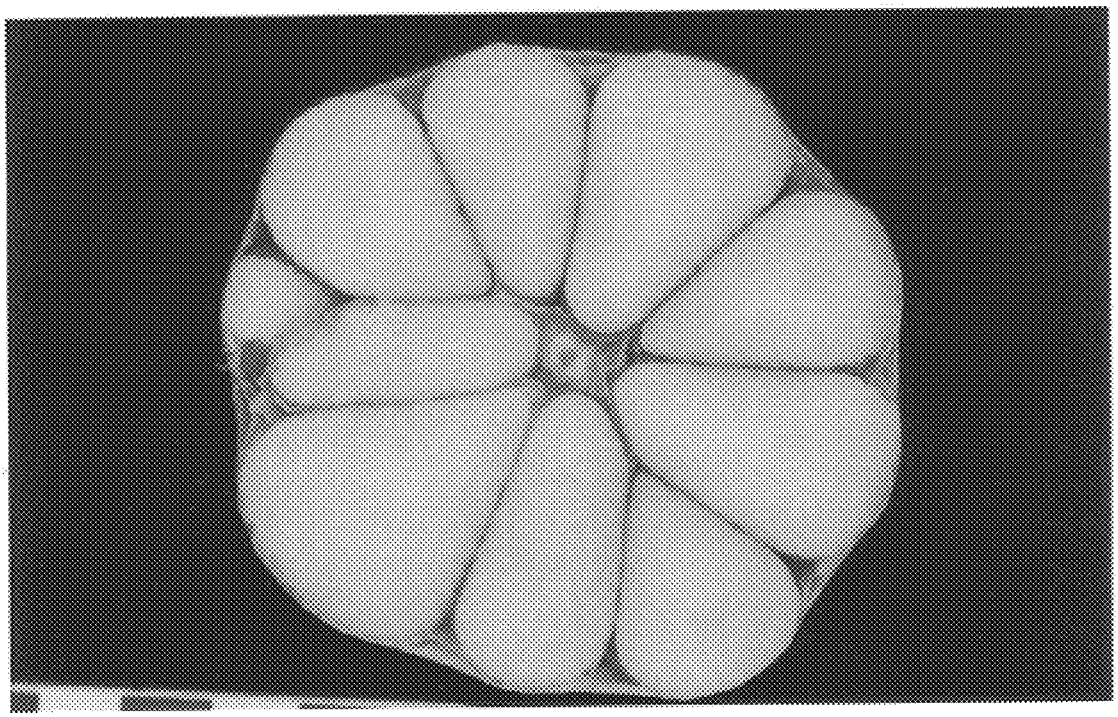

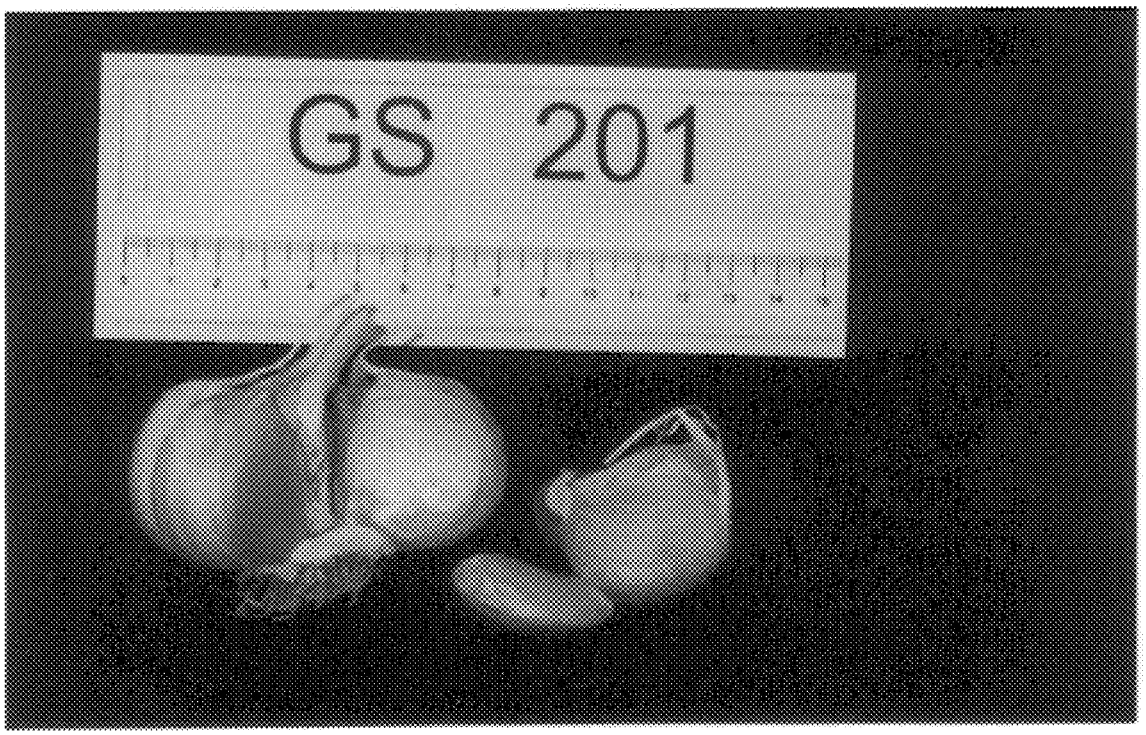
GS 201